US00PP16159P2

(12) United States Plant Patent
Lemon

(10) Patent No.: US PP16,159 P2
(45) Date of Patent: Dec. 13, 2005

(54) GERANIUM PLANT NAMED 'MAESTRO PINK'

(50) Latin Name: *Pelargonium×hortorum*
Varietal Denomination: Maestro Pink

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 33 days.

(21) Appl. No.: 10/946,163

(22) Filed: Sep. 21, 2004

(51) Int. Cl.[7] ..... A01H 5/00
(52) U.S. Cl. ..... Plt./328
(58) Field of Search ..... Plt./328

*Primary Examiner*—Kent Bell
(74) *Attorney, Agent, or Firm*—The Webb Law Firm

(57) ABSTRACT

'Maestro Pink' is a new variety of geranium having a compact habit, early and free flowering, very good outdoor performance, and brightly colored watermelon pink flowers.

1 Drawing Sheet

Botanical classification: *Pelargonium×hortorum.*
Varietal denomination: 'Maestro Pink'.

BACKGROUND OF THE INVENTION

The present invention comprises a new and distinct cultivar of *Pelargonium×hortorum* known by the varietal name 'Maestro Pink', Breeder No. 6DG4071-8. The new variety was discovered in Lompoc, Calif. The new variety is a result of cross breeding 'American Pink' (female parent) (U.S. Plant Pat. No. 8,029) and Seedling 2483 (male parent) (unpatented). The new variety exhibits similar flower color to both parents, but blooms earlier and has a more compact habit than both parents. The new variety was first asexually reproduced by cuttings in Connellsville, Pa. The new variety has been trial and field tested and has been found to retain its distinctive characteristics and remain true to type through successive asexual propagations.

The new variety was grown in a glass greenhouse in Connellsville, Pa. using full light, 60° F. night temperature and 68° F. day temperature and grown in a soilless media with constant fertilizer at 200–250 ppm nitrogen and potassium. The new variety exhibits rooting at 14 days under optimal conditions and has a response time of seven weeks from a rooted cutting to flowering.

DESCRIPTION OF THE DRAWING

The accompanying photographic drawing illustrates the new variety, with the color being as nearly true as is possible with color illustrations of this type.

DESCRIPTION OF THE PLANT

Figure 1:
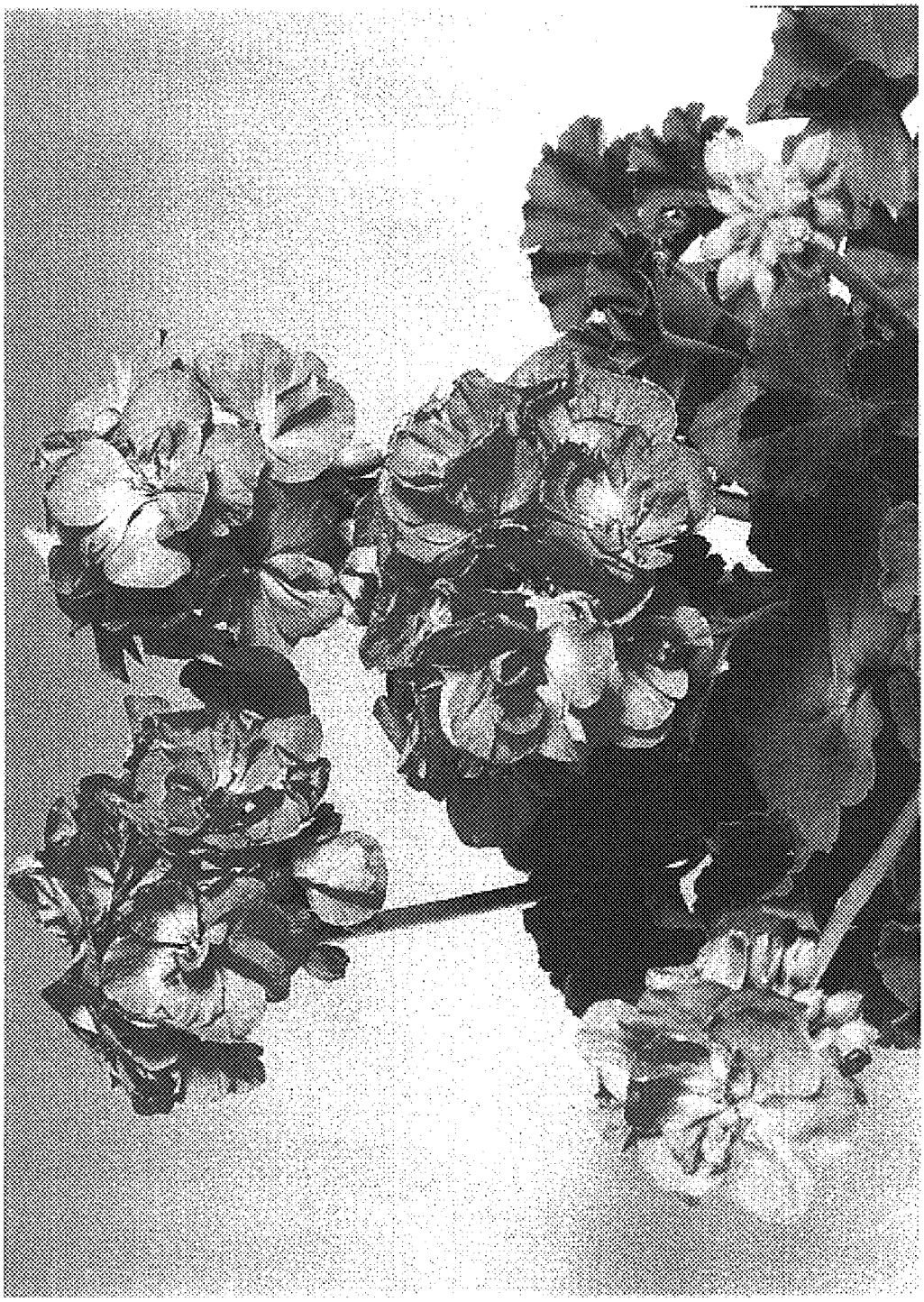

The following detailed description sets forth the characteristics of the new cultivar. The data which defines these characteristics were collected by asexual reproductions carried out in Connellsville, Pa. Plants described were 9 weeks old. The color readings were taken indoors under 65–85 foot candles of cool white fluorescent light. Color references are primarily to The R.H.S. Colour Chart of The Royal Horticultural Society of London.

PLANT

Form: Medium mound.
Growth: Upright mound, with free basal branching.

Height from media surface: 15–17 cm in a 4 inch pot from the top of the soil to the top of the plant.
Strength: Does not require artificial support.
Rooting time: 10–14 days to visible roots on the outside of a plug under optimal conditions.
Foliage: Stalked leaf attachment of a medium green color with zonation present.
Leaves:
- *Arrangement.*—Alternate.
- *Size.*—5.0–7.0 cm long at longest point; 7.3–10.8 cm across at widest point.
- *Zone.*—Present 1.8–2.3 cm from point of attachment; the zone is 1.7–2.0 cm wide.
- *Shape.*—Reniform, with a cordate base.
- *Margin.*—Crenate.
- *Texture.*—Velvety in general. Older leaves are more leathery.
- *Pubescence.*—Present.
- *Color.*—Upper surface: 137B. Lower surface: 138B. Zone: 139A on younger leaves. The zone is less pronounced on older leaves and is 137A.
- *Ribs and veins.*—Type: Palmate. Color: 146D.
- *Stipules.*—Two per node.

Petioles:
- *Color.*—144A.
- *Length.*—4.5–7.0 cm.

Stem:
- *Color.*—144A.
- *Internode length.*—1.7–2.4 cm.

THE BUD (Characteristics measured just before anthesis)

- *Shape.*—Cluster: Elliptical when no color is showing, having 13–16 buds per cluster. Individual bud: Elliptical or oval when no color is showing.
- *Size.*—Cluster: 4.1–5.1 cm across. Individual bud: 0.7–0.9 cm long, 0.5–0.7 cm wide.

INFLORESCENCE

Blooming habit: Continuous; free and early blooming.
Umbel size: 9.5–11.0 cm across.
Borne: Umbel; flowers on pedicel; pedicel on peduncle; 7.0–9.0 cm above foliage.
Number of flowers per umbel: 19–25.

Flowers:

*Form.*—Slightly cupped; petals overlap and petaloids give a ruffled appearance.

*Size.*—4.0–5.1 cm across; 1.7–2.0 cm deep.

*Petals.*—Shape: Inverted teardrop. Size: 2.7–2.9 cm across; 2.4–2.7 cm long. Margin: Entire. Number per flower: 5–7. Texture: Smooth; velvety; highly reflective. Tonality from a distance: Bright candy watermelon pink flower head with a striking stark white center above a mound of medium green foliage. Color: Upper petals have a stark white eye, lower petals lack the eye. Upper surface: Lower petals: 68A at outer edge moving to 68B at middle of petal and fading to 68C, then to 62D, and then to white, about 155A, at the petal base. Upper petals: 68A at outer edge moving to 73C at middle of petal and then to white, about 155A, from middle to the base. Pink veining of 68B is present. Lower surface: Lower petals: 68C at very outer edge fading quickly to 68D and then to 69A. Darker veining of 68C and 68D shows through. At times the veining is darker to 68A. Upper petals: 68C at very outer edge fading quickly to 68D and then to 69A, and then fading to white, about 155A. Veining of 64C and 68B is present.

Petaloids:

*Number.*—0–4.

*Shape.*—Irregular; some are twisted; tubular; petal-shaped with cut margin; anther-like holding pollen.

*Color.*—Same as petals.

Pedicel:

*Length.*—2.8–3.4 cm.

*Color.*—145A at flower base, moving towards 144B near the base of the flower, with accent pigmentation of 184C.

Peduncle:

*Length.*—10.8–16.2 cm.

*Color.*—144A, with slight accent pigmentation of 184C at some spots.

Disease/pest resistance: No susceptibility to diseases or pests has been noted to date.

Lasting quality: Overall blooming habit is continuous throughout the flowering season. Individual umbels last 7–14 days depending on weather conditions.

REPRODUCTIVE ORGANS

Stamens:

*Anthers.*—2.5–3.0 mm long.

*Filaments.*—Length: 6–9 mm. Color: White with watermelon pink tips.

*Pollen color.*—Golden orange.

Pistils:

*Number.*—One.

*Length.*—1.0–1.3 cm.

*Stigma.*—Number: One. Color: 63A.

*Style.*—Length: 4.0–5.0 mm. Color: 63A.

Ovaries:

*Completeness.*—Superior. Length: 5.0–6.0 mm. Width: 2.5–3.0 mm. Color: Green. Pubescence: Present.

Fruit: None observed.

I claim:

1. A new and distinct variety of Geranium plant named 'Maestro Pink' as described and illustrated.

* * * * *